(12) United States Patent
Mastri et al.

(10) Patent No.: US 9,962,520 B2
(45) Date of Patent: May 8, 2018

(54) BRANCHING MULTI-LUMEN TUBE SET FOR LAPAROSCOPIC SURGICAL PROCEDURES INVOLVING SMOKE EVACUATION

(71) Applicant: SurgiQuest, Inc., Milford, CT (US)

(72) Inventors: Dominick Mastri, Bridgeport, CT (US); Kenneth Blier, Cheshire, CT (US)

(73) Assignee: Surgiquest, Inc., Milford, CT (US)

( * ) Notice: Subject to any disclaimer, the term of this patent is extended or adjusted under 35 U.S.C. 154(b) by 646 days.

(21) Appl. No.: 14/514,857

(22) Filed: Oct. 15, 2014

(65) Prior Publication Data

US 2016/0106952 A1  Apr. 21, 2016

(51) Int. Cl.
*A61M 25/00* (2006.01)
*A61M 13/00* (2006.01)
(Continued)

(52) U.S. Cl.
CPC ....... *A61M 25/003* (2013.01); *A61B 17/3423* (2013.01); *A61M 1/0031* (2013.01); *A61M 1/0056* (2013.01); *A61M 1/0058* (2013.01); *A61M 1/0066* (2013.01); *A61M 13/003* (2013.01); *A61M 13/006* (2014.02); *A61M 25/0026* (2013.01); *A61B 17/00234* (2013.01); (Continued)

(58) Field of Classification Search
CPC .. A61M 13/00; A61M 25/003; A61M 13/006; A61M 1/0058; A61M 1/0056; A61M 25/0026; A61M 1/0031; A61M 1/0066; A61M 13/003; A61M 2210/1021; A61B 2218/008; A61B 2218/007; A61B 17/3423; A61B 17/00234; A61B 17/3474; A61B 17/3421

See application file for complete search history.

(56) References Cited

U.S. PATENT DOCUMENTS 6,458,076 B1   10/2002 Pruitt
6,544,210 B1 *  4/2003 Trudel .................. A61B 18/00
                                                                604/26

(Continued)

FOREIGN PATENT DOCUMENTS

DE     102012110889 A1   5/2014
WO    WO-2014039633 A1   3/2014

OTHER PUBLICATIONS

International Search Report and Written Opinion dated Dec. 18, 2015 in related application PCT/US2015/055481.

(Continued)

*Primary Examiner* — Lauren P Farrar
(74) *Attorney, Agent, or Firm* — Locke Lord LLP; Scott D. Wofsy

(57) ABSTRACT

A multi-lumen tube set is disclosed for use during a laparoscopic surgical procedure performed within a patient's abdominal cavity, which includes at least a first lumen configured to extend between a first surgical access port accessing the patient's abdominal cavity and an external vacuum source, and a branching conduit communicating with the first lumen and configured for connection to a second surgical access port accessing the patient's abdominal cavity to facilitate smoke evacuation from the patient's abdominal cavity during a laparoscopic surgical procedure.

10 Claims, 4 Drawing Sheets

(51) Int. Cl.
*A61M 1/00* (2006.01)
*A61B 17/34* (2006.01)
*A61B 17/00* (2006.01)

(52) U.S. Cl.
CPC ....... *A61B 17/3421* (2013.01); *A61B 17/3474* (2013.01); *A61B 2218/008* (2013.01); *A61M 2210/1021* (2013.01)

(56) References Cited

U.S. PATENT DOCUMENTS

| | | |
|---|---|---|
| 7,182,752 B2 | 2/2007 | Stubbs et al. |
| 7,285,112 B2 | 10/2007 | Stubbs et al. |
| 7,338,473 B2 | 3/2008 | Campbell et al. |
| 7,413,559 B2 | 8/2008 | Stubbs et al. |
| 7,854,724 B2 | 12/2010 | Stearns et al. |
| 8,715,219 B2 | 5/2014 | Stearns et al. |
| RE44,972 E | 7/2014 | Matula et al. |
| 8,795,223 B2 | 8/2014 | Stearns et al. |
| 2007/0000300 A1 | 1/2007 | Diemunsch et al. |
| 2010/0185139 A1* | 7/2010 | Stearns .............. A61B 17/3474 604/26 |
| 2012/0150101 A1 | 6/2012 | Stearns et al. |
| 2013/0231606 A1 | 9/2013 | Stearns et al. |
| 2014/0171855 A1 | 6/2014 | Mastri et al. |

OTHER PUBLICATIONS

International Search Report dated Dec. 11, 2013 in connection with PCT/US2013/058192.

\* cited by examiner

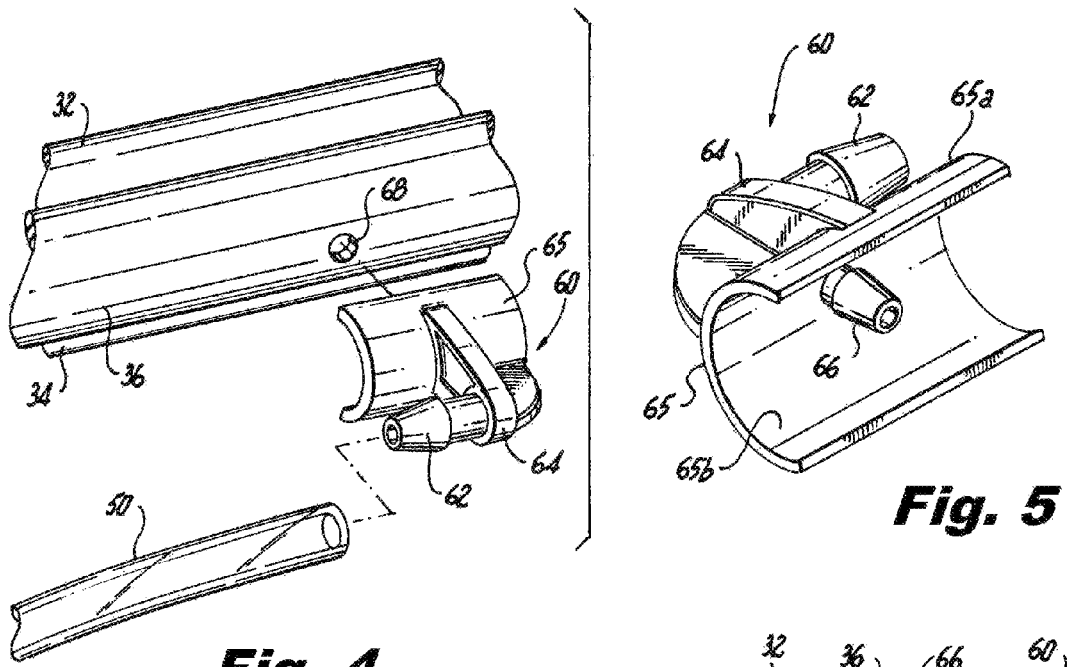
Fig. 4
Fig. 5
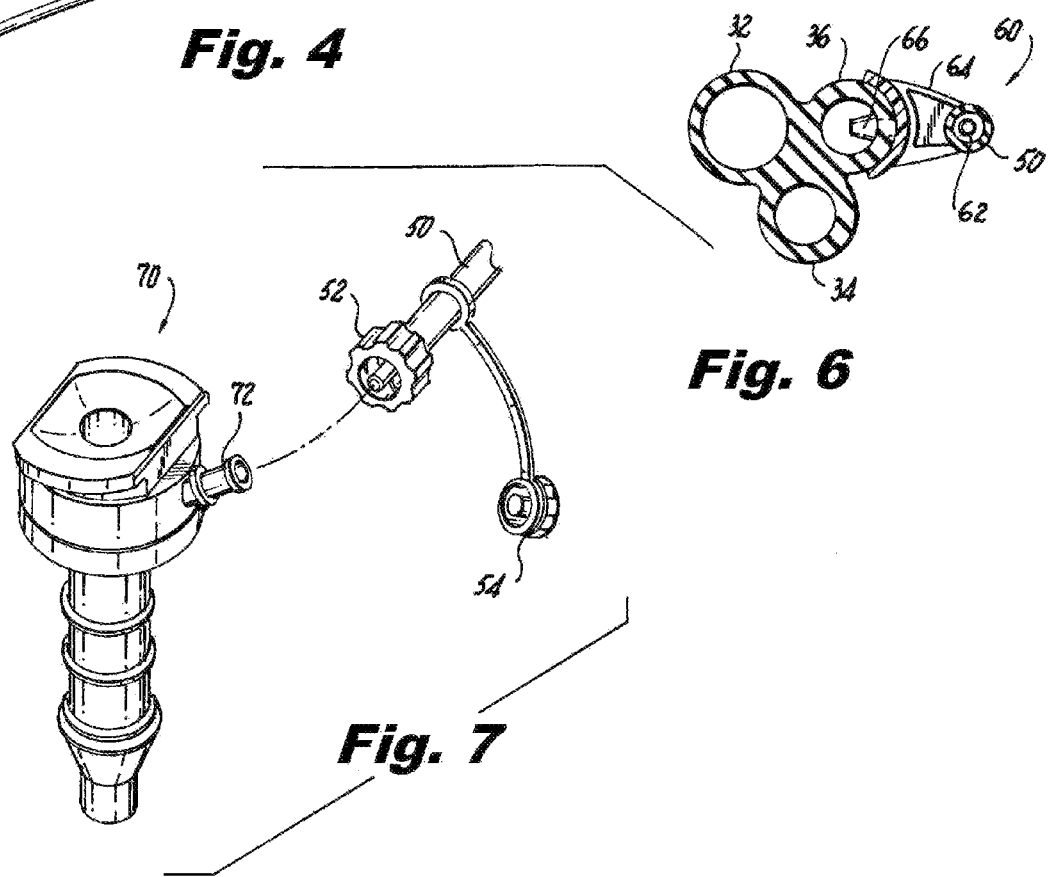
Fig. 6
Fig. 7

BRANCHING MULTI-LUMEN TUBE SET FOR LAPAROSCOPIC SURGICAL PROCEDURES INVOLVING SMOKE EVACUATION

BACKGROUND OF THE INVENTION

1. Field of the Invention

The subject invention is directed to laparoscopic surgery, and more particularly, to a multi-lumen tube set for use with a multimodal insufflation and gas recirculation system used during laparoscopic surgical procedures involving smoke evacuation.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art. The subject invention addresses conditions that arise within the abdominal cavity during a smoke evacuation procedure.

Additionally, SurgiQuest, Inc., Milford, Conn. USA has developed surgical access devices that permit access to an insufflated surgical cavity without conventional mechanical seals, and has developed related systems for providing sufficient pressure and flow rates to such access devices, as described in commonly assigned U.S. Pat. No. 7,854,724 and U.S. Pat. No. 8,715,219, the disclosures of which are herein incorporated by reference in their entireties The present invention relates to gas delivery systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices, as well as those in commonly assigned U.S. Pat. Nos. 7,182,752, 7,285,112, 7,338,473 or 7,413,559 or 8,795,223, each of which are incorporated herein by reference.

Use of a single multimodal gas delivery system along with the multi-lumen tube set described herein improves the operating environment within the abdominal cavity by drawing smoke away from the primary surgical site to improve visualization. It also reduces costs by requiring purchase of only one system while achieving multiple functions, and also thereby reduces the amount of equipment needed in an operating room, thus reducing clutter and allowing space for other necessary equipment.

SUMMARY OF THE INVENTION

The subject invention is directed to a new and useful multi-lumen tube set for use during a laparoscopic surgical procedure performed within a patient's abdominal cavity. The tube set includes at least a first lumen configured to extend between a first surgical access port accessing the patient's abdominal cavity and an external vacuum source. The tube set further includes a branching conduit communicating with the first lumen and configured for connection to a second surgical access port accessing the patient's abdominal cavity to facilitate smoke evacuation from the patient's abdominal cavity during a laparoscopic surgical procedure.

The tube set also includes a second lumen for directing a flow of insufflation gas to an insufflation path of the first surgical access port, wherein the first surgical access port facilitates the introduction of surgical instruments through an instrument path thereof. The tube set also includes a third lumen for directing pressurized gas to a plenum chamber of the first surgical access port to produce a gaseous seal within the instrument path of the surgical access port to prevent the egress of insufflation fluid/gas from the abdominal cavity of the patient.

The first lumen of the tube set is adapted to withdraw spent gas delivered from the plenum chamber of the first surgical access port into the instrument path of the first surgical access port, by way of the suction generated by the external vacuum source.

A proximal or rearward end portion of the branching conduit of the tube set is connected to a communication fitting operatively associated with the first lumen of the tube set. A distal or forward end portion of the branching conduit has a coupling for connection with a fitting on the second surgical access port. More particularly, the coupling on the distal end portion of the branching conduit is adapted and configured to mate with a leur type fitting on the second surgical access port.

The communication fitting that connects the branching conduit and the first lumen of the tube set is supported on a flange that extends radially outwardly from an exterior surface of a semi-cylindrical saddle configured to straddle an exterior surface portion of the first lumen. The communication fitting communicates with a probe that projects radially inwardly from an interior surface of the saddle, and is configured to extend through an aperture in a wall of the first lumen.

A proximal end portion of the tube set is connected to a disposable filter unit or cartridge, and a distal end portion of the tube set is operatively associated with a rotatable coupling configured to connect the tube set to the plenum chamber housing of the first surgical access port. Preferably, the branching conduit has a length that is sufficient to provide adequate spacing between the first and second surgical access ports, so that smoke evacuation through the second surgical access port occurs at an appropriate distance from the first surgical access port.

Preferably, the fluid path through the communication fitting is dimensioned so that the amount of gas/fluid drawn through the branching conduit by the pump assembly will not affect the stability of the pneumoperitoneum maintained by the gas delivery system during a surgical procedure involving smoke evacuation.

The subject invention is also directed to a multi-lumen tube set that includes a first lumen for directing a flow of insufflation gas to an insufflation path of a first surgical access port accessing the patient's abdominal cavity, wherein the first surgical access port facilitates the introduction of instruments through an instrument path thereof, a second lumen for directing pressurized gas to a plenum chamber of the first surgical access port to produce a gaseous seal within the instrument path of the first surgical access port, a third lumen for withdrawing spent gas delivered from the plenum chamber of the first surgical access port under vacuum, and a branching conduit in communication with the third lumen for connecting to a second surgical access port accessing the patient's abdominal cavity to facilitate smoke evacuation from the patient's abdominal cavity during a laparoscopic surgical procedure.

These and other features of the multi-lumen tube set of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the multi-lumen tube set of the subject invention without undue experimentation, preferred embodiments thereof will be described in detail herein below with reference to certain figures, wherein:

FIG. 4 is a localized perspective view of the tube set, with parts separated from one another for ease of illustration, to illustrate the connection between the gas return lumen and the branching conduit of the tube set;

FIG. 5 is a perspective view of the connective fitting structure that facilitates gaseous communication between the gas return lumen and the branching conduit of the tube set;

FIG. 6 is a cross-sectional view taken along line 6-6 of FIG. 3, illustrating the interior passages of the multi-lumen tube set, as well as the interaction between the probe of the communication fitting and the interior of the gas return lumen; and FIG. 7 is a perspective view of a surgical access port and the associated connection at the distal end of the branching conduit of the tube set.

DETAILED DESCRIPTION OF PREFERRED EMBODIMENTS

It is to be appreciated that the systems, devices and methods presented herein may be used for surgical gas delivery, including insufflation, smoke evacuation, and/or recirculation in connection with suitable surgical devices, and in applicable surgical procedures. The present invention is particularly suited for minimizing the amount of equipment needed in a surgical operating room, in that the subject systems are capable of performing multiple functions, and therefore also allow flexibility of surgical technique. It is envisioned that the gas delivery system disclosed herein can be used in general laparoscopic procedures including but not limited to laparoscopic cholecystectomy, laparoscopic appendectomy, laparoscopic hernia repair, Nissen-Y and Lap Nephrectomy.

Those skilled in the art will readily appreciate that systems described in U.S. Pat. Nos. 7,854,724 and 8,715,219, for example, provide pressurized gas to and remove depressurized gas from specialized surgical access devices, which penetrate into a surgical cavity, such as a patient's abdominal cavity. These access devices are adapted and configured to form a pressure barrier to inhibit the loss of insufflation gas to the atmosphere.

Gas from the abdomen interchanges with gas coming from the access device(s), a portion of which is collected and recycled through the system, and is re-pressurized, passing through one or more filters along the way. During this recycling process, smoke and/or other circulating debris, such as atomized fluids, are removed from the recirculating gas flow by the filters, improving visibility within the surgical cavity, thus aiding in the surgical procedure.

Figure 1:
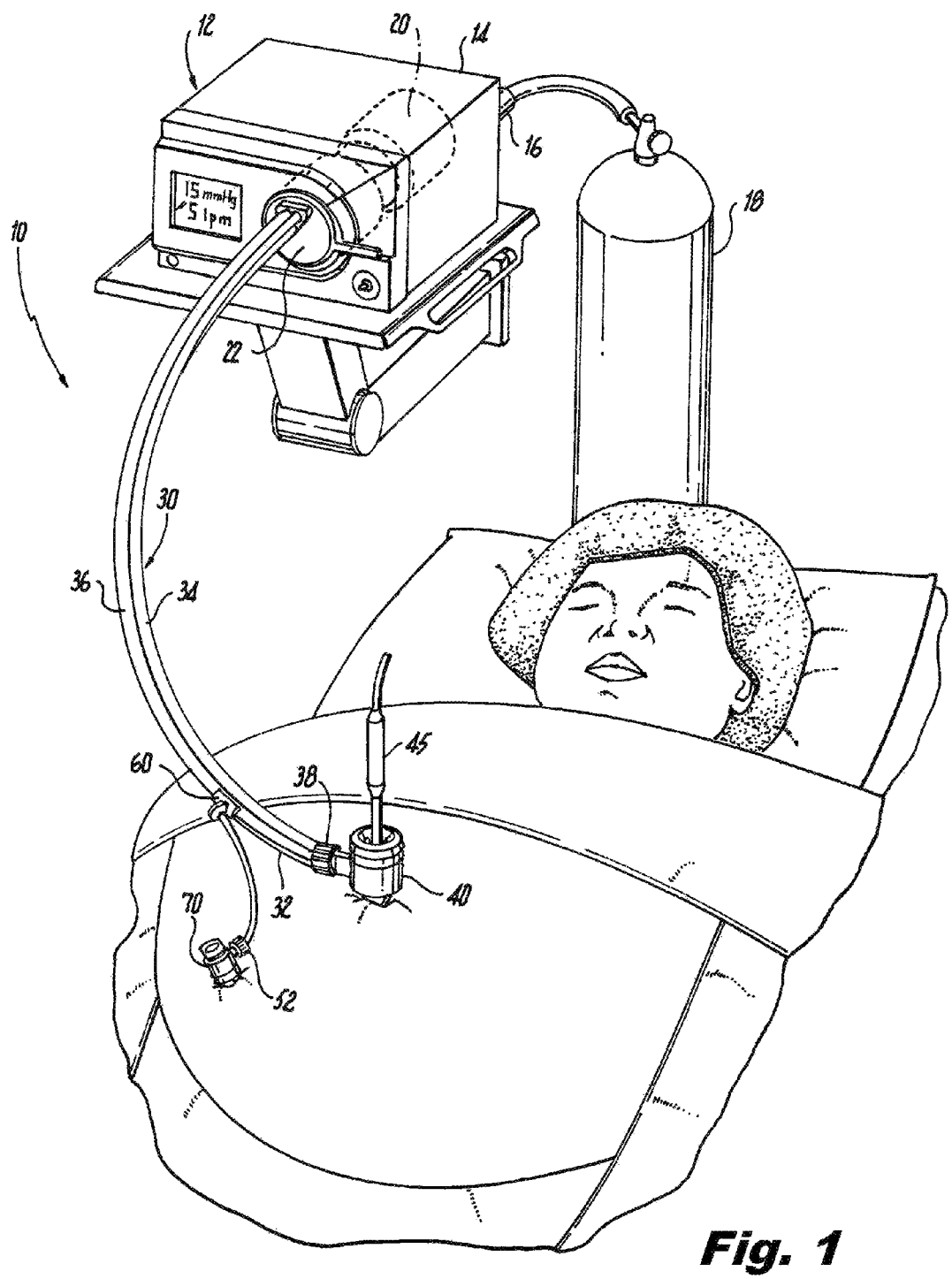
FIG. 1 is an illustration of the multi-lumen tube set of the subject invention in use during a laparoscopic surgical procedure involving smoke evacuation from the abdominal cavity of a patient.

Referring now to the drawings, wherein like reference numerals identify similar structural features or aspects of the subject invention, there is illustrated in FIG. 1 a new and useful system 10 for delivering gas during a laparoscopic surgical procedure performed within a patient's abdominal cavity involving smoke evacuation. The gas delivery system 10 includes, among other things, a gas delivery device 12 having a housing 14 with a port 16 for receiving pressurized insufflation gas from a gas source 18.

A pump assembly 20 is located within the housing 14 of gas delivery device 12 for circulating and recirculating gas/fluid throughout the system 10. A separate removable and disposable gas conditioning unit or filter 22 is also provided for operative association with the housing 14 of the gas delivery device 12. The manner in which the filter unit 22 is received and operatively associated with the housing 14 is described in greater detail in commonly assigned U.S. Patent Application Publication 2013/0231606, the disclosure of which is incorporated herein by reference in its entirety.

Filter unit 22 is of the type that is disclosed, for example, in commonly assigned U.S. Reissued Pat. No. RE44972, as well as commonly assigned U.S. Patent Application Publication 2012/0150101, the disclosures of which are both incorporated herein by reference in the entirety. These filters have multiple independent flow paths and filtration elements for conditioning the pressurized gas/fluid circulating through the gas delivery system 10.

Figure 3:
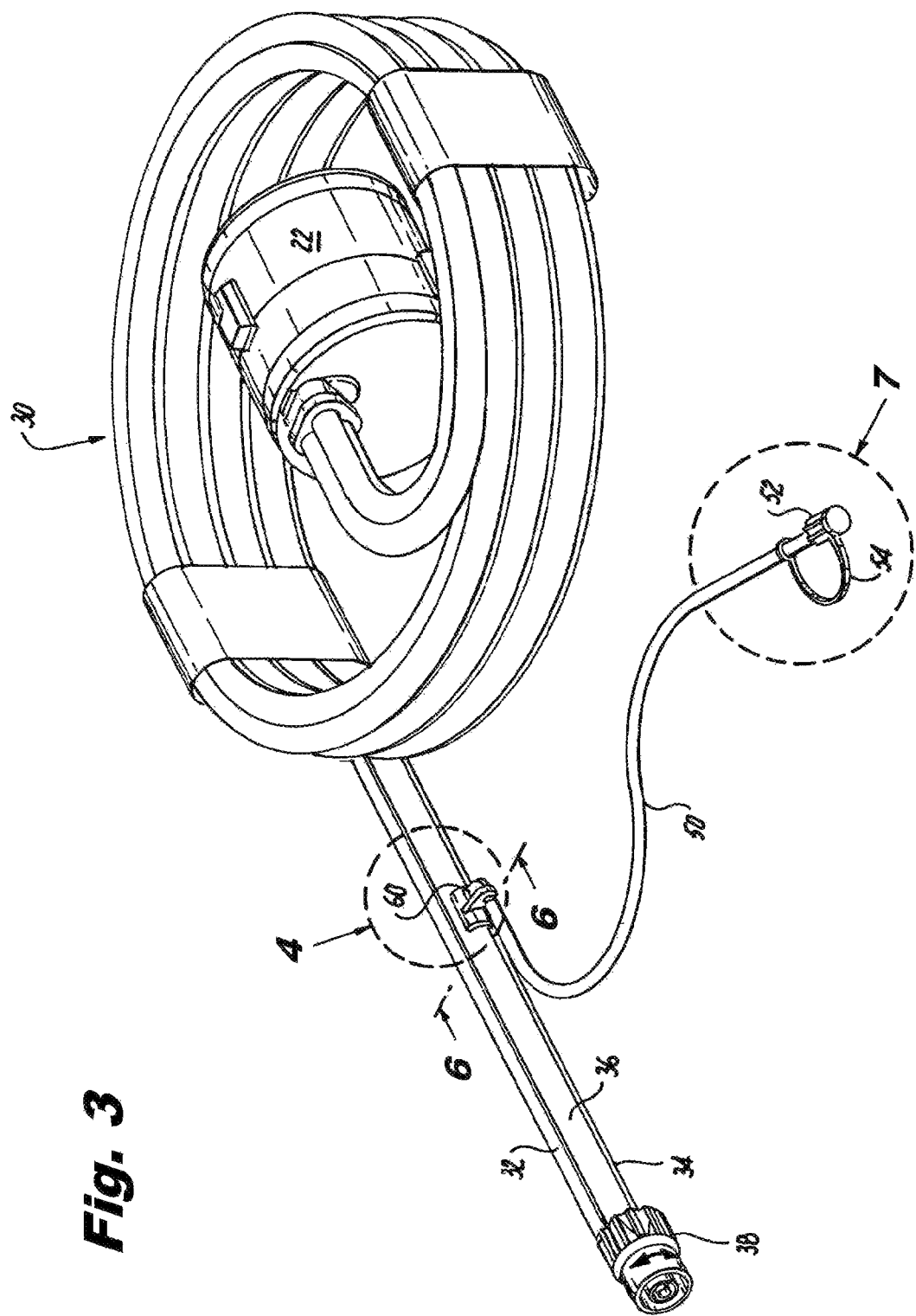
FIG. 3 is a perspective view of the multi-lumen tube set of the subject invention.

The gas delivery system 10 of the subject invention also includes a multi-lumen tube set 30 that is operatively connected to the filter unit 22 for effectuating the circulation and recirculation of pressurized gas/fluid, which is best seen in FIG. 3. The tube set 30 is formed from an extrusion that includes three conjoined flexible tubes or lumens 32, 34 and 36. The three lumens 32, 34 and 36 extend from filter unit 22 to a rotatable coupling 38 that detachably connects the tube set 30 to a primary surgical access port or trocar 40. The rotatable coupling 38 is of the type disclosed for example in commonly assigned U.S. Patent Application Publication 2014/0171855, the disclosure of which is incorporated by reference in its entirety.

Figure 2:
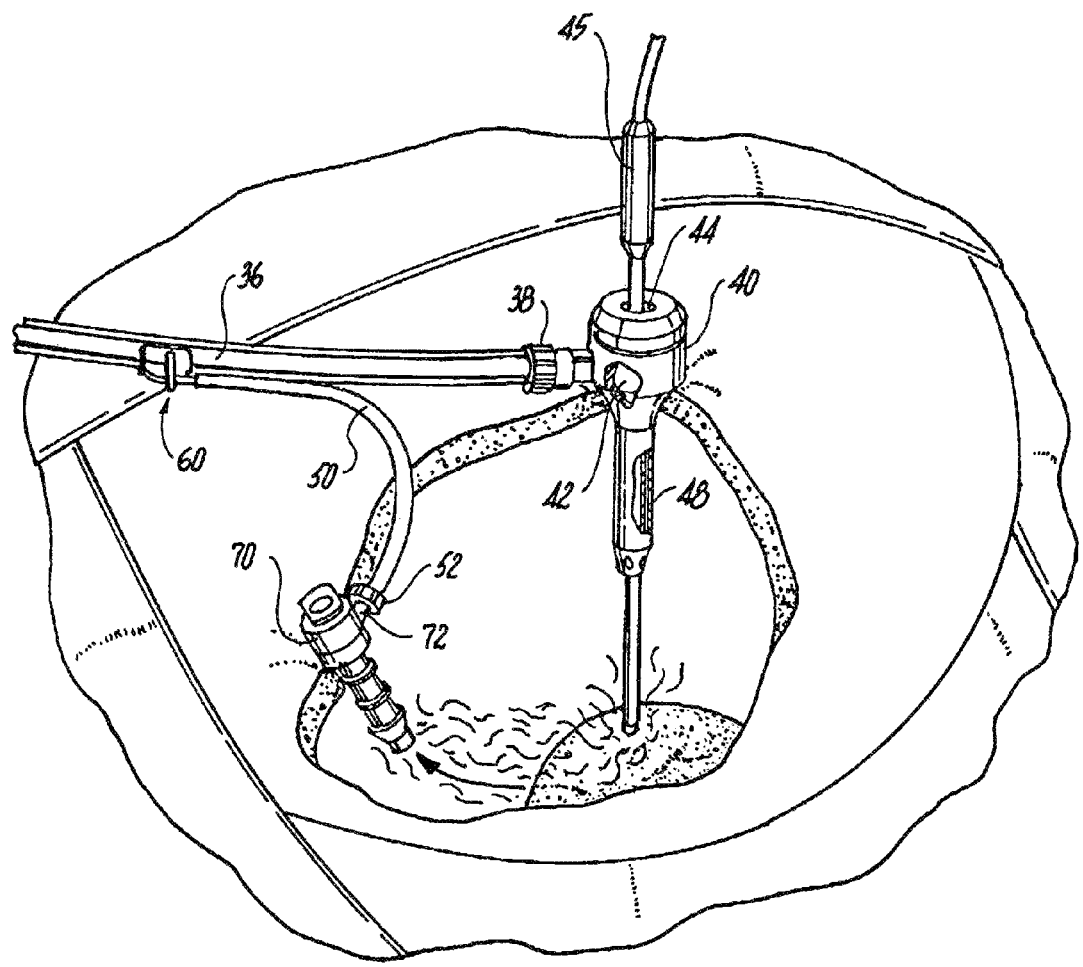
FIG. 2 is an illustrates the evacuation of smoke from the patient's abdominal cavity using the multi-lumen tube set of the subject invention.

The primary surgical access device or trocar 40 is of the type that is disclosed, for example, in commonly assigned U.S. Pat. No. 8,715,219, the disclosure of which is incorporated herein by reference in its entirety. As best seen in FIG. 2, trocar 40 includes, among other things, a plenum chamber 42 for receiving pressurized gas/fluid from the pump assembly 20 in the housing 14 of gas delivery device 12.

The surgical access device or trocar 40 provides ready access to the patient's abdominal cavity through an instrument delivery path 44 for surgical devices such as, for example, a multi-lumen endoscope 45. The multi-lumen endoscope 45 can provide direct visualization of the surgical site while enabling the direct introduction of tools to the surgical site. An example of such a device is disclosed in U.S. Pat. No. 6,458,076, which includes, among other things, a plurality of image guides to facilitate direct visualization of the surgical site and a large central lumen to facilitate the introduction tools to the surgical site. Such tools would include for example, an electrocautery tool for cauterizing tissue. Auxiliary lumens are also provided in device 45 to facilitate irrigation, drug delivery and other functions.

With continuing reference to FIGS. 1 and 2 in conjunction with FIG. 3, lumen 32 of tube set 30 is a pressurized gas delivery lumen that communicates with the positive pressure side or outlet of pump assembly 20 in the housing 14 of gas delivery device 12. More particularly, lumen 32 communicates with the outlet side of pump assembly 20 through an isolated flow path in filter unit 22 to deliver pressurized gas/fluid from the pump assembly 20 to the plenum chamber 42 of trocar 40. This pressurized gas/fluid is used to generate a gaseous seal within an instrument delivery path 44 of the trocar 40 to inhibit the egress of insufflation gas from the abdominal cavity of the patient during a surgical procedure.

Lumen 34 of tube set 30 is a insufflating/sensing lumen that communicates with the gas source 18 connected to the port 16 in housing 14 of gas delivery device 12. More particularly, lumen 34 communicates with the gas source 18 through an isolated flow path in filter unit 22 to deliver insufflating gas to the abdominal cavity of the patient through an internal insufflation channel 48 in trocar 40. In addition, lumen 34 is used to provide a sensing path that enables the gas delivery device 12 to measure static abdominal pressure on a periodic basis, without the flow of insufflating gas therethrough.

Lumen 36 of tube set 30 is a gas return lumen that communicates with the suction/vacuum or inlet side of pump assembly 20 in housing 14 of gas delivery device 12. More particularly, lumen 36 communicates with the inlet side of pump assembly 20 through an isolated flow path in filter unit 22 to receive spent gas/fluid from the instrument delivery path 44 of the trocar 40. The spent gas/fluid is the pressurized gas/fluid from the pump assembly 20 that has lost momentum within the plenum chamber 42 of trocar 40 after generating the gaseous seal in the delivery path 44.

With continuing reference to FIGS. 1 and 2 in conjunction with FIG. 3, the tube set 30 of the subject invention further includes a flexible branching tube or conduit 50 that communicates directly with gas the return lumen 36. Thus, the branching tube or conduit 50 is in fluid communication with the source of vacuum or suction in the system 10 (i.e., the suction side of pump assembly 20). More particularly, branching conduit 50 communicates with gas return lumen 36 through a communication fitting 60 that is described in more detail hereinbelow with reference to FIGS. 4 through 6.

As best seen in FIG. 2, branching conduit 50 is configured for connection to a secondary surgical access port 70 accessing the patient's abdominal cavity at a location spaced apart from the primary surgical access port or trocar 40. In particular, branching conduit 50 includes a leur-type coupling 52 for connecting with an inlet fitting 72 of secondary surgical access port 70 (see FIG. 7). Access port 70 is provided to facilitate smoke evacuation from the patient's abdominal cavity during a laparoscopic surgical procedure. The leur-type coupling 52 of branching conduit 50 can include an optional tethered safety cap 54, as shown.

With continuing reference to FIG. 2, the branching conduit 50 has a length that is sufficient to provide adequate spacing between the primary surgical access port 40 and the secondary surgical access port 70, so that smoke evacuation through the secondary surgical access port 70 during a surgical procedure occurs at an adequate distance from the primary surgical access port 40. This will ensure that the primary surgical space is free of smoke and debris, enabling the surgeon to better visualize the operating environment while cauterizing tissue.

Referring now to FIGS. 4 through 6, the communication fitting 60 that connects the branching conduit 50 to the gas return lumen 36 includes a conically tapered stem 62 supported on a flange 64. Supporting flange 64 extends radially outwardly from an exterior surface 65a of a semi-cylindrical saddle 65, which is adapted and configured to straddle an exterior surface portion of the gas return lumen 36. The communication fitting 60 communicates with a probe 66 that projects radially inwardly from an interior surface 65b of the saddle 65. The probe 66 is adapted and configured to extend through an orifice 68 formed in the a wall of the gas return lumen 36.

Preferably, the fluid path through the communication fitting 60 is dimensioned or otherwise configured so that the branching conduit 50 can only draw a maximum of about 3 L/min of gas/fluid from the abdominal cavity of the patient during a laparoscopic surgical procedure. This physical restriction will ensure that a stable pneumoperitoneum is maintained by the gas delivery system 10 during a surgical procedure involving smoke evacuation.

Referring once again to FIGS. 1 and 2, in use, during a laparoscopic surgical procedure, when a surgeon cauterizes tissue using the multi-purpose endoscopic tool 45, smoke is typically created within the abdominal cavity. That smoke tends to degrade or otherwise obscure the surgical site, inhibiting direct visualization of the surgical site through the optical features of the tool 45. Thus, it becomes necessary to remove the smoke from the abdominal cavity.

Because there is 3 L/min of suction being drawn through the secondary access port 70 under the vacuum of pump assembly 20, the smoke and other debris is drawn away from the site of the cauterization and back through the branching conduit 50. The smoke and debris drawn through conduit 50 then travels through the gas return conduit 36 to the filter unit 22, where it is filtered or otherwise conditioned, and sent back to the pump assembly 20 in housing 14 for recirculation to the plenum chamber 42 of trocar 40.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A multi-lumen tube set for use during a laparoscopic surgical procedure performed within a patient's abdominal cavity, comprising:
   a) at least a first lumen configured to extend between a first surgical access port accessing the patient's abdominal cavity and a filter cartridge communicating with an external vacuum source; and
   b) a branching conduit communicating with the first lumen and configured for connection to a second surgical access port accessing the patient's abdominal cavity to facilitate smoke evacuation from the patient's abdominal cavity during a laparoscopic surgical procedure, wherein the branching conduit communicates with the first lumen at a location between the filter cartridge and the first surgical access port through a communication fitting having a semi-cylindrical saddle adapted and configured to straddle an exterior surface portion of the first lumen, wherein a tapered stem supported on a flange extends radially outward from an exterior surface of the saddle to connect with a proximal end of the branching conduit and a tapered probe projects radially inward from an interior surface of the saddle to extend through an orifice in a wall of the first lumen.

2. A multi-lumen tube set as recited in claim 1, further comprising a second lumen for directing a flow of insufflation gas to an insufflation path of the first surgical access port, wherein the first surgical access port facilitates the introduction of surgical instruments through an instrument path thereof.

3. A multi-lumen tube set as recited in claim 2, further comprising a third lumen for directing pressurized gas to a plenum chamber of the first surgical access port to produce a gaseous seal within the instrument path thereof.

4. A multi-lumen tube set as recited in claim 3, wherein the first lumen is adapted to withdraw spent gas delivered from the plenum chamber of the first surgical access port into the instrument path, by way of suction generated by the external vacuum source.

5. A multi-lumen tube set as recited in claim 3, wherein a distal end portion of the tube set is operatively associated with a rotatable coupling configured to connect the tube set to a housing of the first surgical access port.

6. A multi-lumen tube set as recited in claim 1, wherein a distal end portion of the branching conduit has a coupling for connection with a fitting on the second surgical access port.

7. A multi-lumen tube set as recited in claim 6, wherein the coupling on the distal end portion of the branching conduit is adapted and configured to mate with a luer-type fitting on the second surgical access port.

8. A multi-lumen tube set for use during a laparoscopic surgical procedure performed within a patient's abdominal cavity, wherein a proximal end portion of the tube set is connected to a filter cartridge, the tube set comprising:
   a) a first lumen for directing a flow of insufflation gas to an insufflation path of a first surgical access port accessing the patient's abdominal cavity, wherein the first surgical access port facilitates the introduction of instruments through an instrument path thereof;
   b) a second lumen for directing pressurized gas to a plenum chamber of the first surgical access port to produce a gaseous seal within the instrument path thereof;
   c) a third lumen for withdrawing spent gas delivered from the plenum chamber into the instrument path of the first surgical access port under vacuum; and
   d) a branching conduit in communication with the third lumen for connecting to a second surgical access port accessing the patient's abdominal cavity to facilitate smoke evacuation from the patient's abdominal cavity during a laparoscopic surgical procedure, wherein a proximal end portion of the branching conduit communicates with the third lumen at a location between the filter cartridge and the first surgical access port through a communication fitting, wherein the first, second and third lumens are integrally formed from an extrusion of three conjoined tubes that extend to a common rotatable coupling that detachably connects the three conjoined tubes to the first surgical access port, and wherein a distal end portion of the branching conduit includes a luer-type coupling that detachably connects the branching conduit to an inlet fitting of the second surgical access port.

9. A multi-lumen tube set as recited in claim 8, wherein the communication fitting includes a tapered stem supported on a flange that extends radially outwardly from an exterior surface of a semi-cylindrical saddle that is configured to straddle an exterior surface portion of the third lumen.

10. A multi-lumen tube set as recited in claim 9, wherein the communication fitting further includes a probe that projects radially inwardly from an interior surface of the saddle, and wherein the probe is configured to extend through an aperture formed in a wall of the third lumen.

* * * * *